(12) United States Patent  
Morris

(10) Patent No.: US 9,177,681 B2
(45) Date of Patent: Nov. 3, 2015

(54) BASE FOR RADIOGRAPHIC DEVICE

(71) Applicant: X-Cel X-Ray Corporation, Crystal Lake, IL (US)

(72) Inventor: William W. Morris, Woodstock, IL (US)

(73) Assignee: X-CEL X-RAY CORPORATION, Crystal Lake, IL (US)

( * ) Notice: Subject to any disclaimer, the term of this patent is extended or adjusted under 35 U.S.C. 154(b) by 64 days.

(21) Appl. No.: 14/230,692

(22) Filed: Mar. 31, 2014

(65) Prior Publication Data
US 2015/0279495 A1 Oct. 1, 2015

(51) Int. Cl.
*H05G 1/02* (2006.01)
*G21K 1/04* (2006.01)

(52) U.S. Cl.
CPC ..................... *G21K 1/046* (2013.01)

(58) Field of Classification Search
CPC ....... G21K 1/046; H05G 1/02; A61B 6/4429; G03B 42/025; G03B 42/04; G03B 42/02
USPC ................. 378/169, 170, 177, 185, 187, 188, 378/193–197
See application file for complete search history.

(56) References Cited

U.S. PATENT DOCUMENTS

| | | | |
|---|---|---|---|
| 3,904,531 A * | 9/1975 | Barrett et al. | 378/181 |
| 4,014,266 A | 3/1977 | Naslund et al. | |
| 4,432,095 A * | 2/1984 | Adelmeyer et al. | 378/181 |
| D273,892 S | 5/1984 | Fenne et al. | |
| 4,532,645 A | 7/1985 | Morris | |
| 4,587,668 A | 5/1986 | Morris | |
| 4,590,378 A | 5/1986 | Platz | |
| 4,752,948 A | 6/1988 | MacMahon | |
| 4,775,994 A | 10/1988 | Kranvogel | |
| 4,887,287 A | 12/1989 | Cobben | |
| 4,989,229 A | 1/1991 | Negrelli et al. | |
| 5,081,662 A | 1/1992 | Warden et al. | |
| 5,283,823 A | 2/1994 | Morris | |
| 5,388,142 A | 2/1995 | Morris | |
| 6,863,439 B2 | 3/2005 | Morris | |
| 7,585,109 B2 | 9/2009 | Denley | |
| 7,587,027 B2 | 9/2009 | Quaas | |

* cited by examiner

Primary Examiner — Courtney Thomas
(74) Attorney, Agent, or Firm — Miller, Matthias & Hull LLP

(57) ABSTRACT

A radiographic device may include a movable carriage disposed in a base and having a tray for holding an image receptor. A platform extending over the base may support the weight of the patient independent of the image receptor. The carriage may permit tray movement in lateral and longitudinal directions, thereby to align a desired portion of the image receptor with the patient target area and x-ray source. A base collimator may have one or more blades that are slidable to cover portions of the image receptor that are not being used in the current image capture process.

20 Claims, 6 Drawing Sheets

BASE FOR RADIOGRAPHIC DEVICE

FIELD OF THE DISCLOSURE

This disclosure generally relates to radiographic imaging systems and methods, and more particularly to bases for holding image receptors used in radiographic imaging systems and methods.

BACKGROUND OF THE DISCLOSURE

Various types of radiographic devices are generally known in the art. A known x-ray unit for podiatry is disclosed in U.S. Pat. No. 4,587,668, which is assigned to the same assignee as the present disclosure. Generally, such x-ray units include a platform upon which are placed the feet of a patient to be x-rayed. The platform is elevated above floor level to allow film cassettes to be positioned in a film well located below the platform. The platform may further include a slot for receiving a vertically oriented film cassette. A radiographic head is mounted on vertical mounting members, which serve to space the radiographic head a desired distance above the foot platform. The vertical mounting members are moveable in both the lateral and longitudinal directions so that x-rays of a patient's feet can be taken from many angles while easily maintaining the same source to image distance (SID).

Some radiographic techniques require the patient to place weight on the subject area as the image is captured. A podiatrist, for example, may require certain foot x-rays to be taken where the patient must stand on top of the image receptor during image capture. In some scenarios, a podiatrist may need multiple different images, such as lateral, medial oblique, and anteroposterior (AP) projections, that may require the patient to be repositioned for each image. Repositioning of feet for different views is often difficult or dangerous for elderly patients or individuals whose balance or ability to move on the platform is impaired due to disease or other conditions, such as arthritis.

More recently, electronic methods (such as direct radiography (DR) and computed radiography (CR)) have been developed to obtain and display radiographic images without the use of film. In DR and CR, a reusable image receptor is used to map radiation levels during a radiographic procedure and store the data electronically. This data can then be used to display a radiographic image. While the image receptors used in DR and CR processes may be convenient and less expensive to use than film, the digital conversion process used to obtain and generate images is more sensitive to inaccuracies in measured radiation levels. Consequently, it is important to properly position the patient relative to the image receptor in order to capture the desired type of radiographic image. Additionally, to obtain weight-bearing images, the patient typically stands directly on the image receptor, making proper positioning of the patient more difficult. Still further, while the use of digital image receptors provides an opportunity to capture multiple images on a single receptor, the patient must be precisely aligned with the desired portion of the image receptor and therefore further repositioning of the patient is needed.

SUMMARY OF THE DISCLOSURE

In accordance with one aspect of the present disclosure, a radiographic device for use with an image receptor may include a base assembly having a frame defining a frame top opening and a platform supported by the frame and extending over the frame top opening, the platform defining a lateral direction and a longitudinal direction substantially perpendicular to the lateral direction, the platform and frame defining a base receptacle disposed below the platform. An arm assembly may have a first end pivotably coupled to the base assembly and a second end, and a radiographic head may be coupled to the arm assembly second end. A carriage assembly may be disposed in the base receptacle and include a tray sized to receive the image receptor, the tray being supported for movement in both the lateral and longitudinal directions.

In accordance with another aspect of the present disclosure, a radiographic device for use with an image receptor may include a base assembly having a frame defining a frame top opening and a platform supported by the frame and extending over the frame top opening, the platform and frame defining a base receptacle disposed below the platform. An arm assembly may have a first end pivotably coupled to the base assembly and a second end, and a radiographic head may be coupled to the arm assembly second end. A tray may be disposed in the base receptacle and sized to receive the image receptor. The device may further include a base collimator assembly having a collimator plate positioned between the platform and the tray and defining a collimator aperture through which radiographic energy is admitted into the base receptacle, a first collimator blade slidable relative to the collimator plate and movable to an extended position in which at least a portion of the first collimator blade is aligned with a first portion of the aperture, and a second collimator blade slidable relative to the collimator plate and movable to an extended position in which at least a portion of the second collimator blade is aligned with a second portion of the aperture.

In accordance with another aspect of the present disclosure, a radiographic device for use with an image receptor may include a base assembly having a frame defining a frame top opening and a platform supported by the frame and extending over the frame top opening, the platform defining a lateral direction and a longitudinal direction substantially perpendicular to the lateral direction, the platform and frame defining a base receptacle disposed below the platform. An arm assembly may have a first end pivotably coupled to the base assembly and a second end, and a radiographic head may be coupled to the arm assembly second end. A carriage assembly may be disposed in the base receptacle and include a tray sized to receive the image receptor, the tray being supported for movement in both the lateral and longitudinal directions. The device may further include a base collimator assembly having a collimator plate positioned between the platform and the tray, the collimator plate defining a collimator aperture through which radiographic energy is admitted into the base receptacle, a first collimator blade slidable relative to the collimator plate and movable to an extended position in which at least a portion of the first collimator blade is aligned with a first portion of the aperture, and a second collimator blade slidable relative to the collimator plate and movable to an extended position in which at least a portion of the second collimator blade is aligned with a second portion of the aperture.

BRIEF DESCRIPTION OF THE DRAWINGS

For a more complete understanding of the disclosed methods and apparatuses, reference should be made to the embodiment illustrated in greater detail on the accompanying drawings, wherein.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION

This disclosure relates to apparatus and methods of positioning a patient relative to an image receptor during radiographic procedures. Radiographic devices may include a base upon which the patient may stand. The base may include a support for bearing the weight of the patient above the receptor. A carriage assembly capable of longitudinal and lateral translation may hold the image receptor. Translation of the carriage assembly permits the image receptor to move into alignment with a target area of the patient while the patient's feet remain stationary, thereby minimizing patient movement. Additionally, a base collimator may be provided to limit the area of the image receptor that is used during image capture which, in combination with the carriage assembly, allows different portions of the same image receptor to capture different images with minimal patient repositioning.

The radiographic device of the present disclosure is similar to those disclosed in U.S. Pat. Nos. 4,587,668 and 6,863,439, which have the same assignee as the present disclosure and are incorporated herein by reference. The primary differences between the present device and those of the '668 and '439 patents lie in a base assembly on which the patient may stand during capture of radiographic images, described in greater detail below with reference to FIGS. 5-9.

Figure 1:
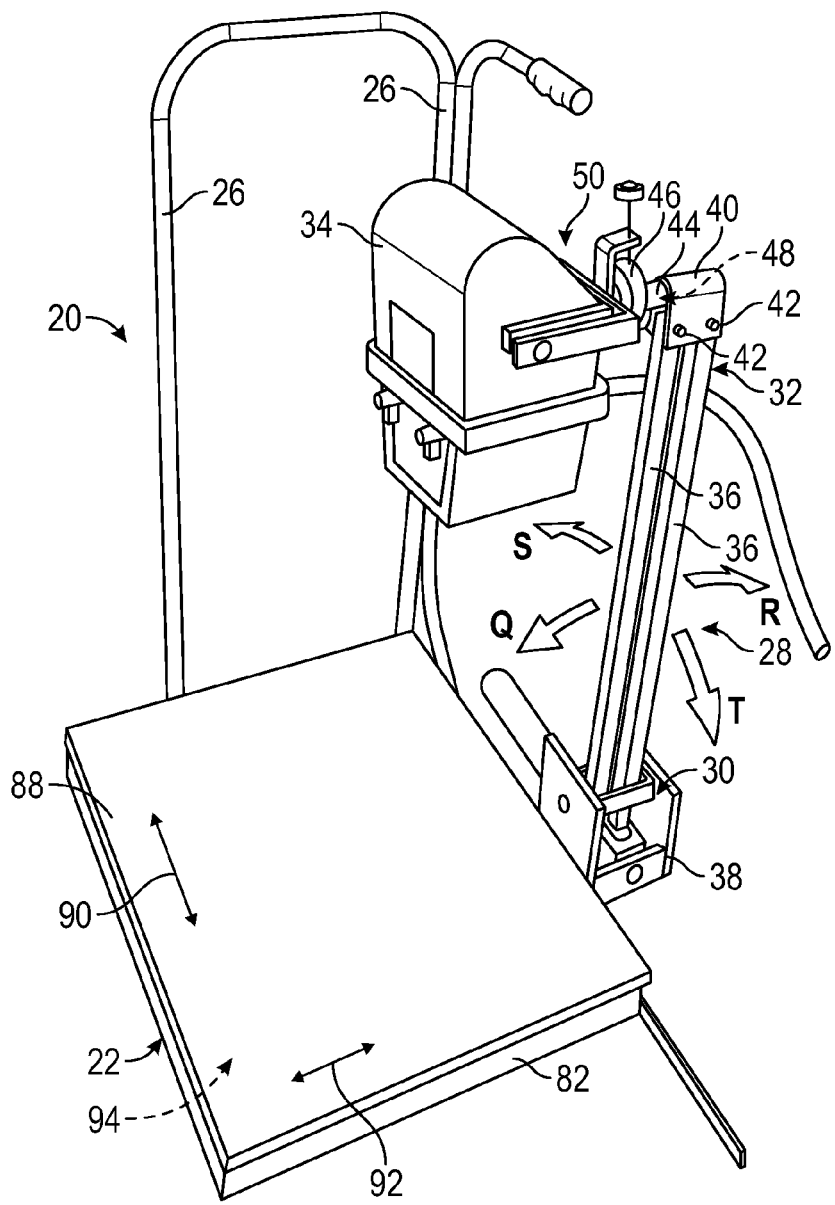
FIG. 1 is a perspective view of a first embodiment of a radiographic device having an adjustable brace constructed in accordance with the teachings of the disclosure.

Referring now to the drawings, and with specific reference to FIG. 1, a radiographic device 20 is described and illustrated herein for use in podiatry treatment, but the teachings provided herein may be applied to radiographic devices used in other fields. The radiographic device 20 includes a base assembly 22 on which a patient may be positioned during image capture. Hand rail legs 26 are mounted to the base assembly 22 and provide a patient support hand rail.

As shown in FIG. 1, a head mounting assembly 28 has a first end 30 pivotably coupled to the base assembly 22 and a second end 32 connected to the radiographic head 34. As used herein, the radiographic head is meant to include a power source and an associated collimator which is attached to and depends from the power source. The power source is capable of emitting electromagnetic radiation sufficient to generate x-ray images. The mounting assembly 28 includes a pair of vertical mounting members 36 having lower ends disposed in a mounting apparatus 38. The mounting apparatus 38 may include spring loaded mounting means for holding the vertical mounting members 36 in a desired position, such as the mounting means disclosed in U.S. Pat. No. 4,587,668 assigned to the current assignee and incorporated herein by reference. Alternatively, other means for holding the vertical mounting members 36 in place may also be used. The upper ends of the vertical mounting members 36 are coupled to a U-shaped mounting plate 40 using bolts 42. A horizontal mounting member 44 has a first end attached to the U-shaped mounting plate 40 and a free second end carrying a collar 46. The horizontal mounting member 44 is hollow to define an internal socket 48.

Figure 2:
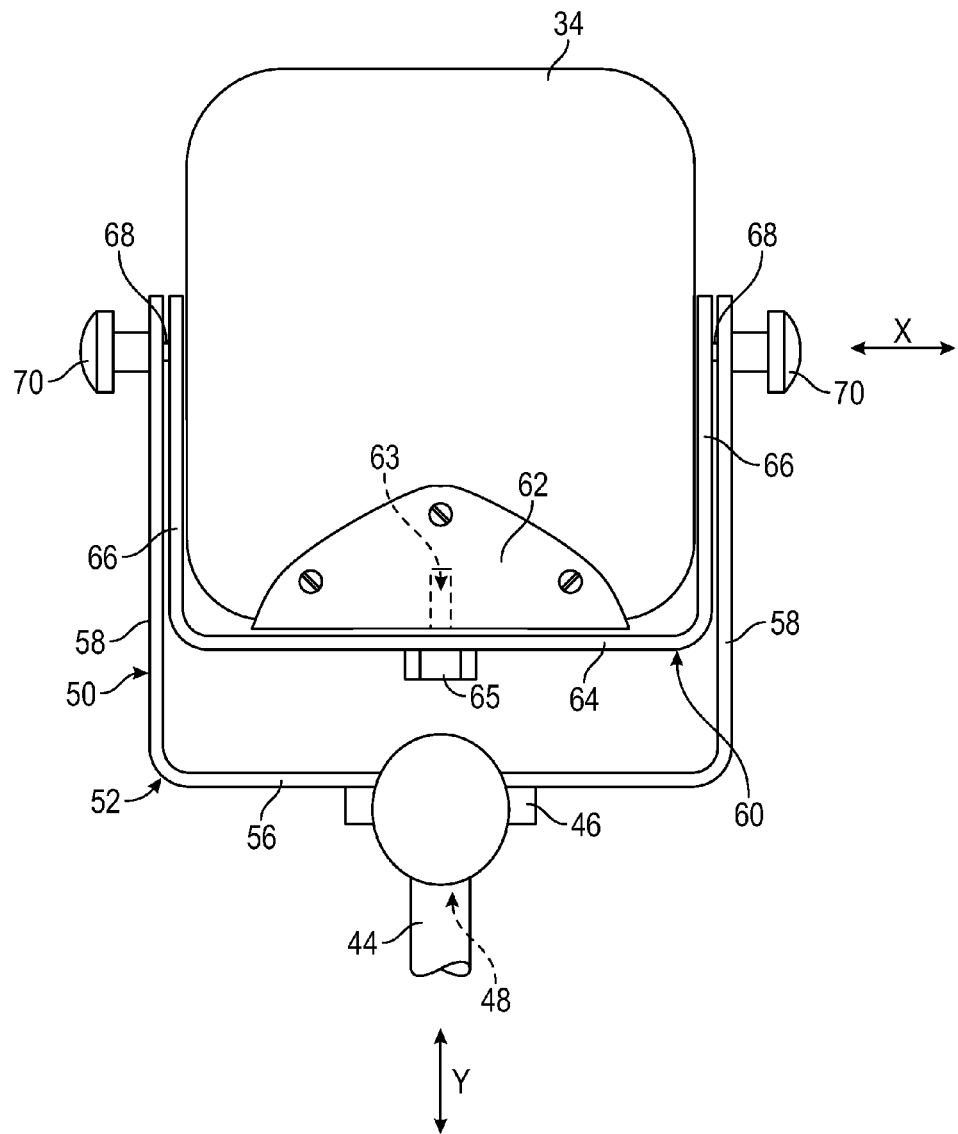
FIG. 2 is an enlarged plan view of a radiographic head used in the radiographic device of FIG. 1.

A yoke 50 is provided for coupling the radiographic head 34 to the mounting assembly 28 and allowing angular adjustment not only about the Y axis, but also about an axis that is parallel to the lateral direction, referred to herein as the X axis (FIG. 2). In the illustrated embodiment, the yoke 50 includes an outer bracket 52 having a stub shaft sized for insertion into the socket 48 of the horizontal member 44. The outer bracket 52 includes a cross support 56 attached to the stub shaft and spaced, generally parallel outer arms 58 attached to opposite ends of the cross support 56.

In the illustrated embodiment, the yoke 50 further includes an inner bracket 60 attached to a back plate 62 of the radiographic head 34. The inner bracket 60 includes a cross member 64 spanning a width of the radiographic head and two inner arms 66 attached to opposite ends of the cross member 64. The inner bracket 60 is sized to closely fit inside the outer bracket 52 so that, when the radiographic head 34 is oriented in the position shown in FIG. 3, the outer arms 58 overlie the inner arms 66. The back plate 62 includes a threaded aperture 63 for receiving a fastener 65. The fastener 65 passes through a hole in the cross member 64 thereby to secure the inner bracket 60 to the radiographic head back plate 62. Pins 68 are attached to the inner arms 66 and pass through holes formed in the outer arms 58 to pivotably couple the inner bracket 60 to the outer bracket 52. Free ends of the pins 68 are threaded to receive knobs 70 which may be rotated to secure the inner bracket 60 and radiographic head 34 at a desired angle with respect to the outer bracket 52.

The outer bracket 52 further includes a set screw assembly having a bracket 72 attached to the cross support 56. A threaded aperture 74 is formed in the bracket 72 and is sized to receive a set screw 76. The set screw 76 has a length sufficient so that an end of the set screw is engageable with the collar 46. As a result, the set screw 76 may be loosened to allow the stub shaft 54 of the yoke 50 to rotate within the socket 48, thereby adjusting the angle of the radiographic head 34 about the X axis. The set screw 76 may then be tightened to engage the collar 46 thereby locking the yoke 50 and attached radiographic head 34 in the desired position.

Figure 3:
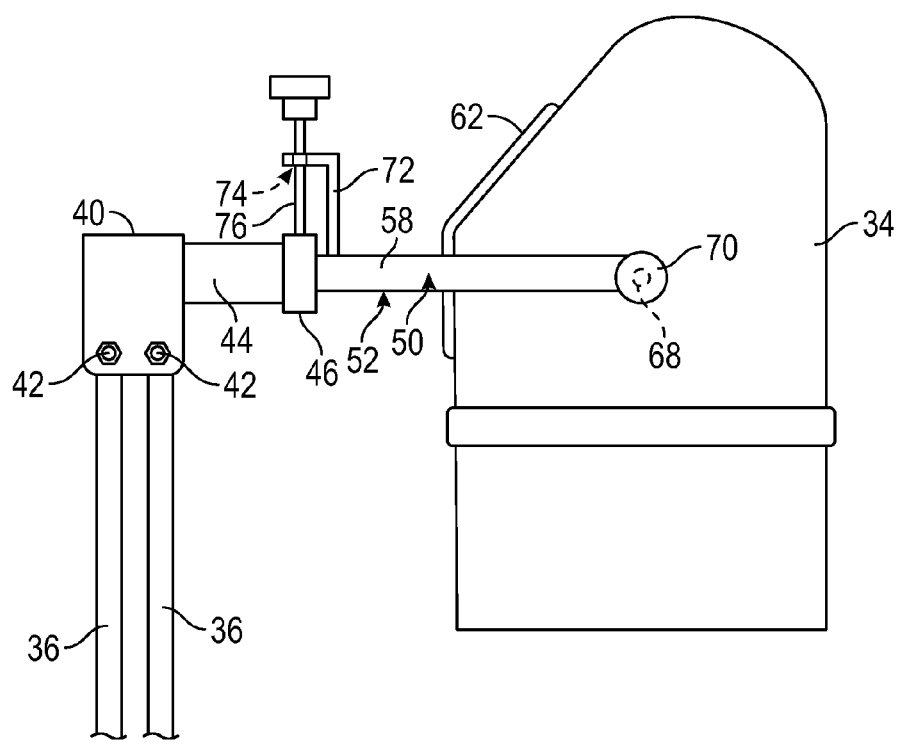
FIG. 3 is an enlarged side view of the radiographic head of FIG. 2 oriented to take a substantially vertical projection.
Figure 4:
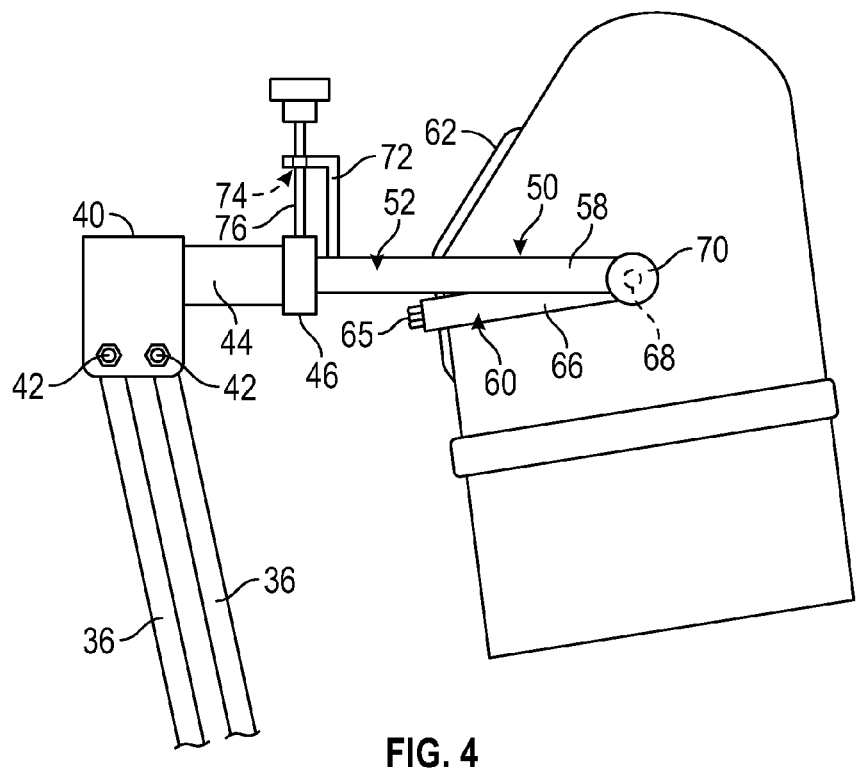
FIG. 4 is an enlarged side view of the radiographic head of FIG. 2 tilted to obtain an angled projection.

The radiographic head 34 described herein permits adjustment of the head for multiple projections. For example, the vertical mounting members 36 may be rotated laterally in directions S or T as shown in FIG. 1 and the radiographic head 34 may be rotated about the Y axis defined by the horizontal mounting member 44 and stub shaft 54 to obtain lateral or medial oblique projections. For these projections, the vertical mounting members 36 form substantially a right angle to the longitudinal direction, as illustrated at FIG. 3. In addition, the vertical mounting members 36 may be rotated longitudinally in directions Q and R and the outer bracket 52 of the yoke 50 may be adjusted to an appropriate angle about the X axis defined by the pins 68 to obtain additional projections such as the AP projection, as illustrated at FIG. 4. The yoke 50 allows the radiographic head 34 to be tilted about the X axis so that the radiographic head 34 is directed to substantially the same target area. While a particular type of adjustable radiographic head 34 is described herein, it will be appreciated that other types of radiographic heads and supports therefor may be used without departing from the scope of the claims.

The base assembly 22 may support any load applied thereto independently of an image receptor 80. The image receptor 80 may be may be any type of receptor, such as a cassette, panel, or film, used to capture images from CR, DR, or other types of radiographic procedures. In the embodiment illustrated in FIGS. 5-9, the base assembly 22 includes a frame 82 which may be formed out of structural components such as steel rectangular tube. The frame 82 may define a frame top opening 84 and a frame side opening 86.

The base assembly 22 may also include a platform 88 (FIG. 1) supported by the frame 82 that extends over the frame top opening 84. As understood more fully below, the platform 88 may be formed of a material that is sufficiently strong to withstand the weight of a patient that is also radiolucent (i.e., partly or wholly permeable to radiation and especially X rays). In some embodiments, for example, the platform 88 may be formed of a thermoplastic polycarbonate having a thickness of approximately ½ inch. The platform 88 may be configured to define a lateral direction 90 and a longitudinal direction 92 that are consistent with the lateral directions S, T and longitudinal directions Q, R of the vertical mounting members 36. When assembled, the frame 82 and platform 88 define a base receptacle 94 disposed below the platform 88.

Figure 5:
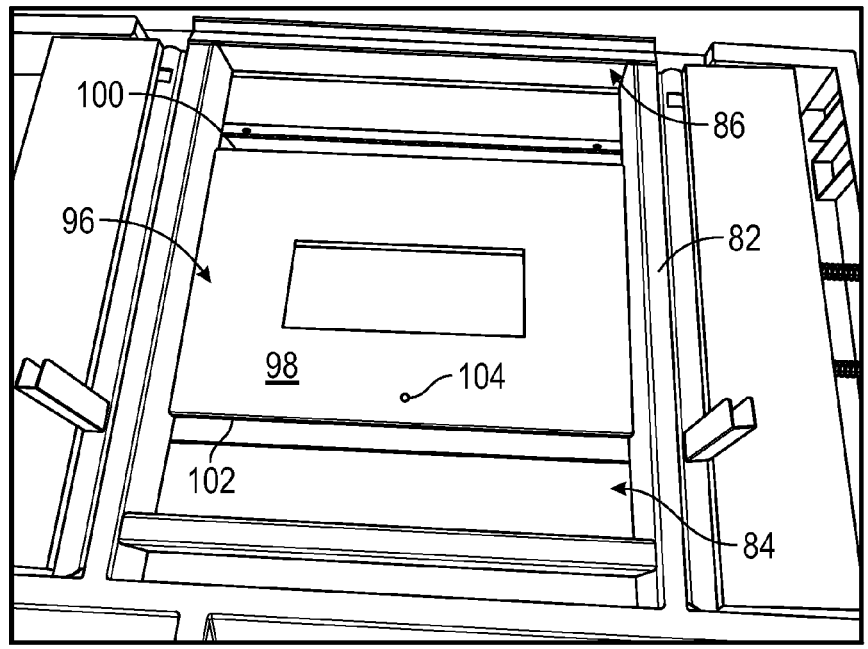
FIG. 5 is a top perspective view of a base assembly used in the radiographic device of FIG. 1 showing a pedestal.

The base assembly 22 may further include a pedestal 96 coupled to the frame 82 and defining a top wall 98. As best shown in FIG. 5, the pedestal 96 may include pedestal side walls 100, 102 extending downwardly from the top wall 98. A pin 104 may project upwardly from the top wall 98.

Figure 6:
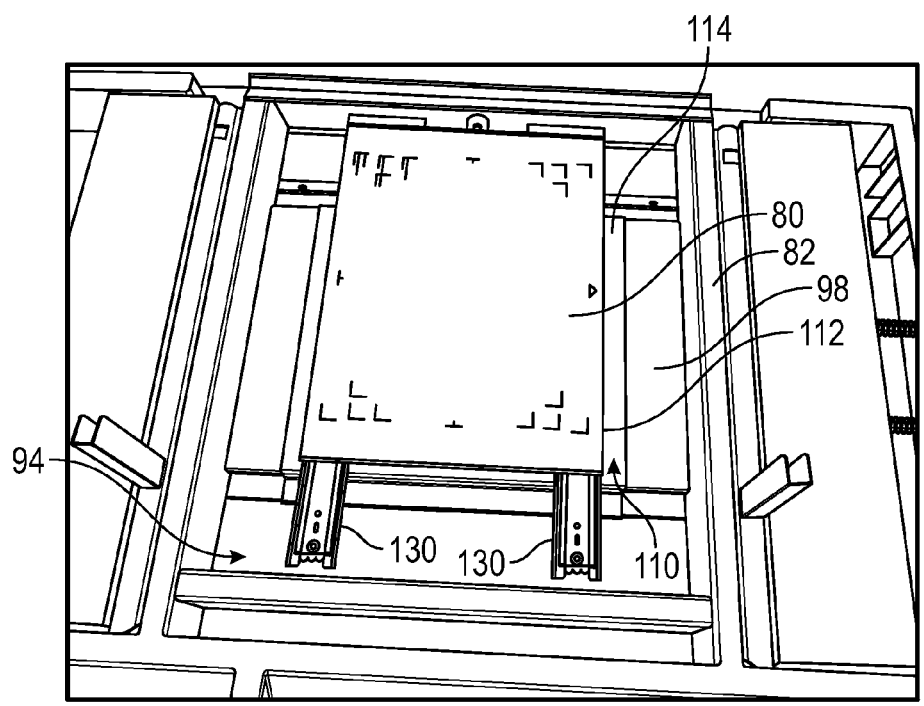
FIG. 6 is a top perspective view of the base assembly of FIG. 5 showing a carriage assembly.

A carriage assembly 110 may be disposed in the base receptacle 94 and may include a tray 112 sized to receive the image receptor 80, as best shown in FIG. 6. The carriage assembly 110 may be supported in a non-weight bearing relationship relative to the patient platform 88. In the illustrated embodiment, the carriage assembly 110 is supported by the frame 82 independently of the platform 88, so that loads applied to the platform 88 are not transferred to the carriage assembly 110. Specifically, the carriage assembly 110 is supported by the platform 98 that is attached to a bottom of the frame 82, while the platform 88 lies over and is supported by a top of the frame 82.

The tray 112 may be supported for movement in multiple directions, such as in both the lateral and longitudinal directions. In the embodiment illustrated in FIGS. 6 and 7, the carriage assembly 110 includes a carrier 114 adapted to slide along the pedestal 96. More specifically, the carrier 114 includes a carrier top plate 116 and carrier side walls 118, 120. The carrier side walls 118, 120 are spaced by a distance to closely fit over the pedestal side walls 100, 102. Accordingly, when the carrier 114 is positioned above the pedestal 96, the close fit of the carrier side walls 118, 120 over the pedestal side walls 100, 102 guide the sliding movement of the carrier 114 (and tray 112 coupled thereto) along the pedestal 96. In the illustrated embodiment, movement of the carrier 114 along the pedestal 96 is in the lateral direction.

Figure 7:
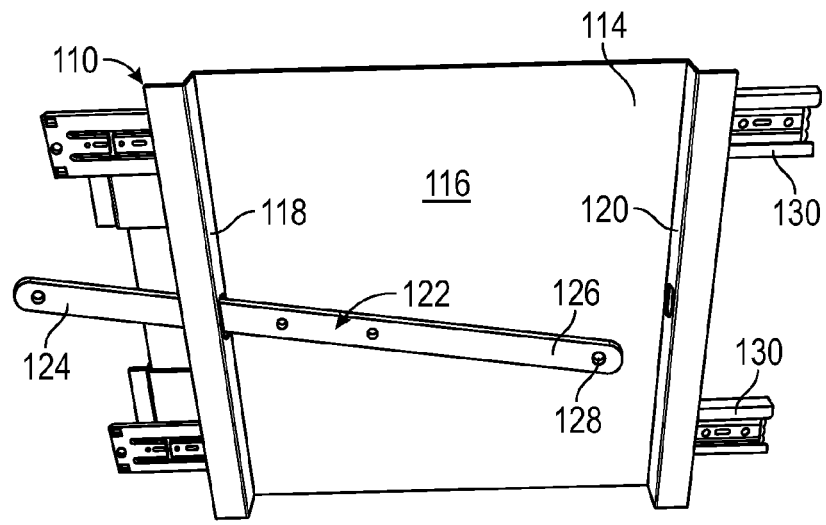
FIG. 7 is a bottom perspective view of the carriage assembly of FIG. 6.

The carrier 114 may further include a lever 122 to allow an operator to manually slide the carrier 114 laterally along the pedestal 96. As best shown in FIG. 7, the lever 122 is pivotably mounted to the carrier 114 and includes a handle end 124 and a connection end 126. The connection end 126 is disposed below the carrier 114 and includes an aperture 128 sized to fit over the pin 104 on the pedestal 96. The handle end 124 extends longitudinally through the frame side opening 86 to permit an operator to grasp and manipulate the lever 122. In operation, when the aperture 128 is fitted over the pin 104, the pin 104 is held in a fixed position by the pedestal 96 so that a lateral force applied to the handle end 124 of the lever 122 will slide the carrier 114 along the pedestal 96.

The carriage assembly 110 may further include one or more slide assemblies 130 to permit movement of the tray 112 in the longitudinal direction. As best shown in FIGS. 6 and 7, the carriage assembly 110 may include two slide assemblies 130, each slide assembly 130 being disposed between the carrier 114 and the tray 112. In the illustrated embodiment, the slide assemblies 130 are provided as roller drawer sliders, however any device that permits translation of the tray 112 relative to the carrier 114 may be used. The slide assemblies 130 may be oriented to permit movement of the tray 112 in the longitudinal direction. In operation, the user may simply grasp the tray 112 and apply a longitudinal force to slide the tray 112 in the longitudinal direction. The slide assemblies 130 may be configured to permit the tray 112 to travel in the longitudinal direction between an image capture position, in which the tray 112 is disposed within the base receptacle 94, and a receptor loading position, in which the tray 112 is positioned at least partially outside of the base receptacle 94. In the illustrated embodiment, the tray 112 passes at least partially through the frame side opening 86 as it moves between the image capture and tray loading positions.

Figure 8:
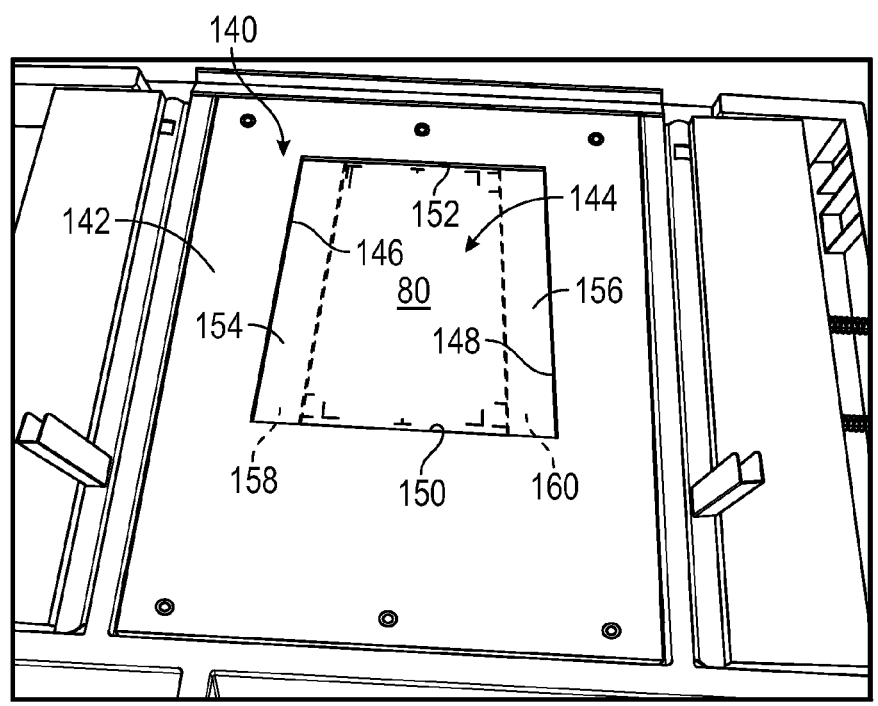
FIG. 8 is a top perspective view of the base assembly of FIG. 5 showing a collimator assembly.
Figure 9:
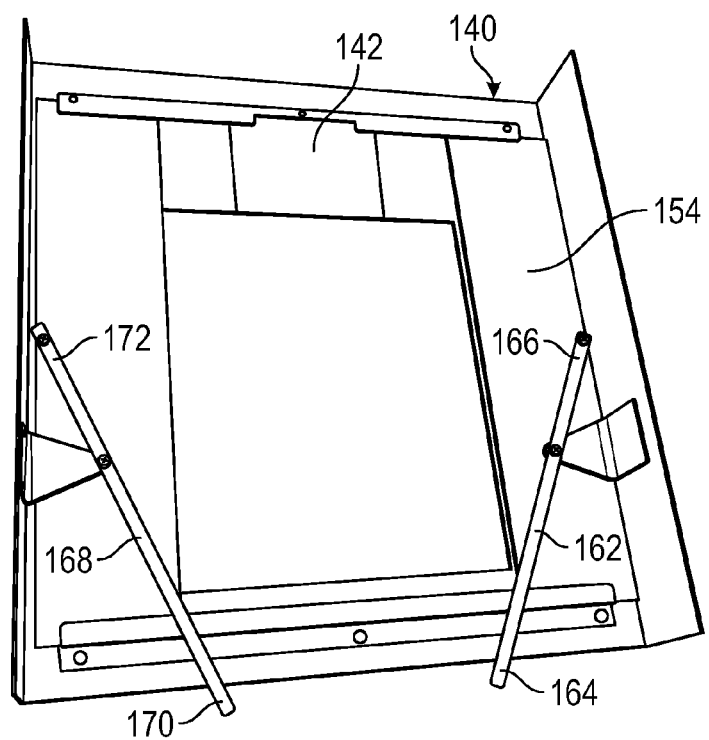
FIG. 9 is a bottom perspective view of the collimator assembly of FIG. 8.

A base collimator assembly 140 may be provided to limit the area of the image receptor 80 that is exposed to radiographic energy during a radiographic procedure, thereby to facilitate the capture of multiple images on a single image receptor 80, as best shown in FIGS. 8 and 9. The base collimator assembly 140 may include a collimator plate 142 positioned between the platform 88 and the tray 112. The collimator plate 142 may define a collimator aperture 144 through which radiographic energy is admitted into the base receptacle 94. In the illustrated embodiment, the collimator aperture 144 has a rectangular shape that includes opposed lateral edges 146, 148 and opposed longitudinal edges 150, 152, however other aperture shapes may be used.

Referring to FIG. 8, the base collimator assembly 140 may further include first and second collimator blades 154, 156 for adjusting the effective size of the collimator aperture 144. The first collimator blade 154 is supported for slidable movement relative to the collimator plate 142 between a retracted position, in which the first collimator blade 154 is positioned outside of the collimator aperture 144, and an extended position, in which at least a portion of the first collimator blade 154 is aligned with a first portion 158 of the aperture located adjacent lateral edge 146. Similarly, the second collimator blade 156 is supported for slidable movement relative to the collimator plate 142 between a retracted position, in which the second collimator blade 156 is positioned outside of the collimator aperture 144, and an extended position, in which at least a portion of the second collimator blade 156 is aligned with a second portion 160 of the aperture located adjacent lateral edge 148. The collimator plate 142 and first and second collimator blades 154, 156 may be formed of a material that is radio-opaque (i.e., not transparent to X-rays or other forms of radiation) to block the passage of radiographic energy and prevent associated portions of the image receptor 80 from being used.

In the illustrated embodiment, the first and second collimator blades 154, 156 are adjustable between the retracted and extended positions independently of each other. As best shown in FIG. 9, a first blade lever 162 is pivotably coupled to the collimator plate 142 and includes a handle end 164 and a connection end 166. The connection end 166 is pivotably coupled to the first collimator blade 154 so that a lateral force applied to the handle end 164 will pivot the first blade lever 162 and move the first collimator blade 154. Similarly, a second blade lever 168 is pivotably coupled to the collimator plate 142 and includes a handle end 170 and a connection end 172. The connection end 172 is pivotably coupled to the second collimator blade 156 so that a lateral force applied to the handle end 170 will pivot the second blade lever 168 and move the second collimator blade 156.

In operation, the carriage assembly 110 may reduce the amount of patient positioning and repositioning needed during radiographic procedures. By providing a separate platform 88 for supporting the weight of the patient and providing the movable carriage assembly 110 to hold the image receptor 80, the position of the image receptor 80 may be adjusted to obtain the desired projection. Minimal movement of the patient, such as side stepping small distances, may be needed to align the foot of interest with the center line of the X-ray source, thereby eliminating the need for the patient to rotate to acquire the same view. Furthermore, multiple different projections may be obtained while the patient remains stationary on the platform 88, thereby further reducing the amount of patient repositioning.

In addition, the base collimator assembly 140 permits multiple different images to be captured on different portions of the same image receptor 80. For example, one or both of the collimator blades 154, 156 may be moved to the extended position to block one or more portions of the collimator aperture 144, thereby reducing the effective area of the collimator aperture 144. The carriage assembly permits the image receptor 80 to be moved so that a first desired portion of the image receptor 80 is aligned with the effective area of the collimator aperture 144. After a first image is captured in the first desired portion of the image receptor, the collimator blades 154, 156 and/or the carriage assembly 110 may be adjusted so that an effective area of the collimator aperture 144 is aligned with a second desired portion of the image receptor that is different than the first desired portion. A second image may then be captured in the second desired portion.

While only certain embodiments have been set forth, alternatives and modifications will be apparent from the above description to those skilled in the art. These and other alternatives are considered equivalents and within the spirit and scope of this disclosure and the appended claims.

What is claimed is:

1. A radiographic device for use with an image receptor, the radiographic device comprising:
    a base assembly including:
        a frame defining a frame top opening; and
        a platform supported by the frame and extending over the frame top opening, the platform defining a lateral direction and a longitudinal direction substantially perpendicular to the lateral direction, the platform and frame defining a base receptacle disposed below the platform;
    an arm assembly having a first end pivotably coupled to the base assembly and a second end;
    a radiographic head coupled to the arm assembly second end; and
    a carriage assembly disposed in the base receptacle and including a tray sized to receive the image receptor, the tray being supported for movement in both the lateral and longitudinal directions.

2. The radiographic device of claim 1, in which the base assembly includes a pedestal coupled to the frame and defining a top wall for supporting the tray.

3. The radiographic device of claim 2, in which the carriage assembly includes a carrier coupled to the tray and slidably disposed on the pedestal to permit movement of the tray in the lateral direction.

4. The radiographic device of claim 3, in which the carriage assembly includes a slide assembly disposed between the carrier and the tray and oriented to permit movement of the tray in the longitudinal direction.

5. The radiographic device of claim 1, further comprising a base collimator assembly including:
    a collimator plate positioned between the platform and the carriage assembly, the collimator plate defining a collimator aperture through which radiographic energy is admitted into the base receptacle; and
    a first collimator blade slidable relative to the collimator plate and movable to an extended position in which at least a portion of the first collimator blade is aligned with a first portion of the aperture.

6. The radiographic device of claim 5, in which the base collimator further includes a second collimator blade slidable relative to the collimator plate and movable to an extended position in which at least a portion of the second collimator blade is aligned with a second portion of the aperture.

7. The radiographic device of claim 6, in which the collimator aperture defines opposed first and second aperture lateral edges adjacent to the first and second portions of the aperture.

8. The radiographic device of claim 6, in which the first collimator blade is movable to the extended position independent of the second collimator blade.

9. The radiographic device of claim 1, in which the carriage assembly is supported in a non-weight bearing relationship relative to the patient platform.

10. The radiographic device of claim 1, in which the carriage assembly is coupled to the frame independently of the platform.

11. The radiographic device of claim 1, in which the frame defines a side opening aligned with the carriage assembly, and in which the tray is movable through the frame side opening to a receptor loading position.

12. A radiographic device for use with an image receptor, the radiographic device comprising:
    a base assembly including:
        a frame defining a frame top opening; and
        a platform supported by the frame and extending over the frame top opening, the platform and frame defining a base receptacle disposed below the platform;
    an arm assembly having a first end pivotably coupled to the base assembly and a second end;
    a radiographic head coupled to the arm assembly second end;
    a tray disposed in the base receptacle and sized to receive the image receptor; and
    a base collimator assembly including:
        a collimator plate positioned between the platform and the tray, the collimator plate defining a collimator aperture through which radiographic energy is admitted into the base receptacle;
        a first collimator blade slidable relative to the collimator plate and movable to an extended position in which at least a portion of the first collimator blade is aligned with a first portion of the aperture; and
        a second collimator blade slidable relative to the collimator plate and movable to an extended position in which at least a portion of the second collimator blade is aligned with a second portion of the aperture.

13. The radiographic device of claim 12, in which the collimator aperture defines opposed first and second aperture lateral edges adjacent to the first and second portions of the aperture.

14. The radiographic device of claim 12, in which the first collimator blade is movable to the extended position independent of the second collimator blade.

15. The radiographic device of claim 12, in which the tray is supported in a non-weight bearing relationship relative to the patient platform.

16. A radiographic device for use with an image receptor, the radiographic device comprising:
a base assembly including:
a frame defining a frame top opening; and
a platform supported by the frame and extending over the frame top opening, the platform defining a lateral direction and a longitudinal direction substantially perpendicular to the lateral direction, the platform and frame defining a base receptacle disposed below the platform;
an arm assembly having a first end pivotably coupled to the base assembly and a second end;
a radiographic head coupled to the arm assembly second end;
a carriage assembly disposed in the base receptacle and including a tray sized to receive the image receptor, the tray being supported for movement in both the lateral and longitudinal directions; and
a base collimator assembly including:
a collimator plate positioned between the platform and the tray, the collimator plate defining a collimator aperture through which radiographic energy is admitted into the base receptacle;
a first collimator blade slidable relative to the collimator plate and movable to an extended position in which at least a portion of the first collimator blade is aligned with a first portion of the aperture; and
a second collimator blade slidable relative to the collimator plate and movable to an extended position in which at least a portion of the second collimator blade is aligned with a second portion of the aperture.

17. The radiographic device of claim 16, in which:
the base assembly includes a pedestal coupled to the frame and defining a top wall for supporting the tray;
the carriage assembly includes a carrier coupled to the tray and slidably disposed on the pedestal to permit movement of the tray in the lateral direction; and
the carriage assembly includes a slide assembly disposed between the carrier and the tray and oriented to permit movement of the tray in the longitudinal direction.

18. The radiographic device of claim 16, in which the collimator aperture defines opposed first and second aperture lateral edges adjacent to the first and second portions of the aperture.

19. The radiographic device of claim 16, in which the first collimator blade is movable to the extended position independent of the second collimator blade.

20. The radiographic device of claim 16, in which the tray is supported in a non-weight bearing relationship relative to the patient platform.

\* \* \* \* \*